United States Patent
Mahmudimanesh et al.

(10) Patent No.: US 9,902,572 B2
(45) Date of Patent: Feb. 27, 2018

(54) METHOD OF CONFIGURING A LABORATORY AUTOMATION SYSTEM, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Mohammadreza Mahmudimanesh, Griesheim (DE); Achim Sinz, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/272,792

(22) Filed: Sep. 22, 2016

(65) Prior Publication Data

US 2017/0096307 A1    Apr. 6, 2017

(30) Foreign Application Priority Data

Oct. 6, 2015 (EP) ..................................... 15188661

(51) Int. Cl.
B65G 54/02 (2006.01)
B65G 19/02 (2006.01)
B65G 43/00 (2006.01)
G01N 35/04 (2006.01)

(52) U.S. Cl.
CPC ............ B65G 54/02 (2013.01); B65G 19/02 (2013.01); B65G 43/00 (2013.01); G01N 35/04 (2013.01); G01N 2035/0465 (2013.01); G01N 2035/0477 (2013.01); G01N 2035/0491 (2013.01); G01N 2035/0493 (2013.01)

(58) Field of Classification Search
CPC .......... G01N 35/04; G01N 2035/0401; G01N 2035/046; G01N 235/0474; G01N 2035/0475; G01N 2035/0489; G01N 35/00; G01N 2035/0491; G01N 2035/0465; G01N 2035/0477; G01N 2035/0493; G01N 2035/0496; B65G 47/74; B65G 43/00; B65G 35/00; B65G 54/02; B65G 19/00; G01D 18/00; G01D 5/145
USPC ..................................... 198/619; 422/63, 65
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |

(Continued)

FOREIGN PATENT DOCUMENTS

| | | | | |
|---|---|---|---|---|
| CH | EP 3153867 A1 | * | 4/2017 | ............ B65G 19/02 |
| CN | 201045617 Y | | 4/2008 | |

(Continued)

*Primary Examiner* — Mark A Deuble
(74) *Attorney, Agent, or Firm* — Roche Diagnostics Operations, Inc.

(57) ABSTRACT

A method of configuring a laboratory automation system is presented. The position of a laboratory station is detected automatically. A laboratory sample distribution system and a laboratory automation system adapted to perform such a method are also presented.

12 Claims, 1 Drawing Sheet

(56) References Cited

U.S. PATENT DOCUMENTS

| | | |
|---|---|---|
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,593,970 B2 * | 3/2017 | Sinz .................. G01R 33/0035 |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |

FOREIGN PATENT DOCUMENTS

| | | |
|---|---|---|
| CN | 102109530 A | 6/2011 |
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |

(56) References Cited

FOREIGN PATENT DOCUMENTS

| | | |
|---|---|---|
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A2 | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 96/36437 A1 | 11/1996 |
| WO | 03/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2012/170636 A1 | 12/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

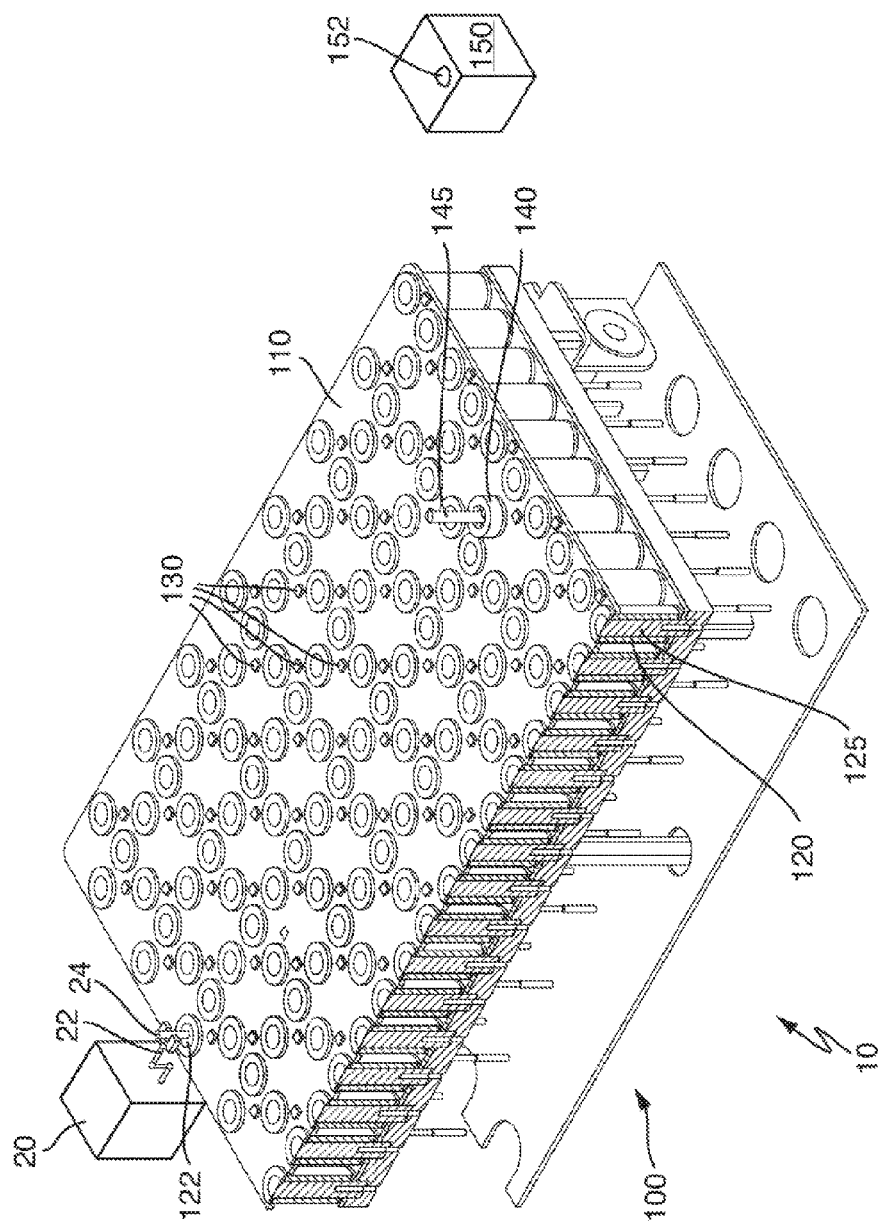

METHOD OF CONFIGURING A LABORATORY AUTOMATION SYSTEM, LABORATORY SAMPLE DISTRIBUTION SYSTEM AND LABORATORY AUTOMATION SYSTEM

CROSS-REFERENCE TO RELATED APPLICATIONS

This application claims priority to EP 15188661.1, filed Oct. 6, 2015, which is hereby incorporated by reference.

BACKGROUND

The present disclosure relates to a system and method of configuring a laboratory automation system, the laboratory automation system comprising a laboratory sample distribution system and at least one laboratory station.

Known laboratory sample distribution systems are typically used in laboratory automation systems in order to transport samples contained in sample containers between different laboratory stations. Such a laboratory sample distribution systems typically provide for a high throughput and for reliable operation.

In order to provide for the possibility to deliver samples or sample containers to laboratory stations using a laboratory sample distribution system, laboratory stations are typically placed adjacent to a transport plane of the laboratory sample distribution system. However, it has been recognized that the laboratory stations have to be placed exactly at a specific position adjacent to the transport plane in order to provide for a reliable transfer of samples or sample containers. As transport planes of sample distribution systems can have quite large dimensions, this requires an accurate metering of large distances in order to position a laboratory station correctly.

Therefore, there is a need for a system and method of configuring a laboratory automation system that allows for easy configuration.

SUMMARY

According to the present disclosure, a method of configuring a laboratory automation system is presented. The laboratory automation system can comprise a laboratory sample distribution system and at least one laboratory station. The laboratory station can have a handover position. The laboratory sample distribution system can comprise a number of sample container carriers adapted to carry one or more sample containers. Each sample container carrier can comprise at least one magnetically active device. The laboratory sample distribution system can also comprise a transport plane adapted to support the sample container carriers, a number of electro-magnetic actuators stationary arranged below the transport plane, the electro-magnetic actuators adapted to move sample container carriers on top of the transport plane by applying a magnetic force to the sample container carriers, a number of position sensors distributed over the transport plane and adapted to sense magnetic fields generated by the magnetically active devices, and a control device configured to control the movement of the sample container carriers on top of the transport plane by driving the electro-magnetic actuators such that the sample container carriers move along corresponding transport paths. The laboratory station can be placed adjacent to the transport plane. The method can comprise placing a reference magnet in a specified position relationship with the handover position of the laboratory station over the transport plane, detecting the position of the reference magnet on the transport plane using the position sensors, and determining one of the electro-magnetic actuators as a handover electro-magnetic actuator based on the detected position.

Accordingly, it is a feature of the embodiments of the present disclosure to provide for a system and method of configuring a laboratory automation system that allows for easy configuration. Other features of the embodiments of the present disclosure will be apparent in light of the description of the disclosure embodied herein.

BRIEF DESCRIPTION OF THE DRAWING

The following detailed description of specific embodiments of the present disclosure can be best understood when read in conjunction with the following drawing, where like structure is indicated with like reference numerals and in which:

FIG. 1 illustrates a laboratory automation system according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method of configuring a laboratory automation system is presented. The laboratory automation system can comprise a laboratory sample distribution system and at least one laboratory station. The laboratory station can have one or more handover positions. The handover position can typically be a position configured to transfer samples or sample containers between the laboratory station and a transport plane located besides the laboratory station or adjacent to the laboratory station. Thus, the handover position can be a position inherent to the laboratory station that can be relevant for interaction with the laboratory sample distribution system.

The laboratory sample distribution system can comprise a number of sample container carriers adapted to carry one or more sample containers. Each sample container carrier can comprise at least one magnetically active device. It can further comprise a transport plane adapted to support the sample container carriers and a number of electro-magnetic actuators. The electro-magnetic actuators can be stationary arranged below the transport plane typically in rows and columns and can be adapted to move a sample container carrier on top of the transport plane by applying a magnetic force to the sample container carrier.

The laboratory sample distribution system can further comprise a number of position sensors typically equally distributed over the transport plane and adapted to sense magnetic fields generated by the magnetically active devices. It can further comprise a control device configured to control the movement of the sample container carriers on top of the transport plane by driving the electro-magnetic actuators such that the sample container carriers move along corresponding transport paths.

The laboratory station can be placed adjacent to the transport plane.

The method can comprise placing a reference magnet in a specified position relationship with the handover position of the laboratory station over the transport plane (e.g. placing the reference magnet exactly at the handover position of the laboratory station). The placing may be performed by an operator manually or automatically by a dedicated device. The method can also comprise detecting the position of the reference magnet on the transport plane using the position sensors and defining or determining one of the electro-magnetic actuators as a handover electro-magnetic actuator based on the detected position.

The above steps may be repeated for each of a plurality of handover positions, if the laboratory station has a plurality of handover positions.

The reference magnet may, for example, be embodied as a permanent magnet.

Alternatively or additionally, an electromagnet can be used. By using an electromagnet, a pattern of bits can be send to the laboratory automation system by turning on and off the electromagnet. The defined or determined handover electro-magnetic actuator may be optically visualized. If, for example, LEDs positioned under a light transmitting transport plane are assigned to the electro-magnetic actuators, the LED assigned to the handover electro-magnetic actuator may be activated.

The determining of one of the electro-magnetic actuators as a handover electro-magnetic actuator based on the detected position may comprise: calculating a distance between (each of) the electro-magnetic actuators and the detected position and determining the electro-magnetic actuator having the minimal distance to the detected position as the handover electro-magnetic actuator.

A handover electro-magnetic actuator can be determined based on the actual position of the laboratory station, basically without manual intervention. For such reason, there can no longer be a need to place the laboratory station at a predetermined position adjacent to the transport plane. In other words, the configuring logic can be inversed. Instead of aligning the laboratory station with respect to the laboratory sample distribution system, the handover electro-magnetic actuator of the laboratory sample distribution system can be aligned with respect to the laboratory station. The laboratory station can be placed adjacent to the transport plane at a basically arbitrary position. The relevant handover position can be determined automatically and the handover electro-magnetic actuator can be selected accordingly. This can significantly reduce the time needed to set up and configure a laboratory automation system.

The handover electro-magnetic actuator can typically be configured or determined such that sample containers or sample container carriers can be moved to the handover electro-magnetic actuator for transfer of samples or sample containers between the laboratory station and the transport plane. In other words, the handover electro-magnetic actuator can be an electro-magnetic actuator selected out of a plurality of electro-magnetic actuators based on the handover position of the laboratory station at its actual place.

The sample containers can typically be designed as tubes made of glass or transparent plastic and typically can have an opening at an upper end. The sample containers can be used to contain, store and transport samples, such as blood samples or chemical samples.

The transport plane can also be denoted as transport surface. The transport plane can support the sample container carriers, what can also be denoted as carrying the sample container carriers.

The electro-magnetic actuators can typically be built as electromagnets, having a solenoid surrounding a ferromagnetic core. These electro-magnetic actuators may be energized in order to provide for a magnetic field that can be used to move or drive the sample container carriers. For that purpose, the at least one magnetically active device in each sample container carrier may be a permanent magnet. Alternatively or additionally, an electromagnet can be used.

The control device can typically be a microprocessor, a microcontroller, a field programmable gate array, a standard computer, or a similar device. In a typical embodiment, the control device can comprise a processor and storage. Program code can be stored in the storage in order to control the behavior of the processor when the storage code is executed on the processor.

The sample container carriers can typically be adapted to move in two dimensions on the transport plane. For that purpose, the electro-magnetic actuators may be arranged in two dimensions below the transport plane. The electro-magnetic actuators may be arranged in a grid or matrix having rows and columns along which the electro-magnetic actuators can be arranged.

According to one embodiment, the position of the reference magnet can be determined in the same way as a position of a sample container carrier. This can allow, for example, for the use of identical algorithms for determining the position of the reference magnet and the sample container carrier. It can be understood that detection of a position of a sample container carrier can be a typical functionality of a laboratory sample distribution system according to the prior art.

According to one embodiment, the position of the reference magnet can be determined by the control device. This can allow for a simple integration of the position determination.

According to an embodiment, the reference magnet can be part of the laboratory station. This can increase accuracy and simplify operation.

According to an embodiment, the reference magnet can be part of a position determining device held by a gripping device of the laboratory station. The position determining device can, for example, be a pen-shaped object having a permanent magnet. Especially, the position determining device can be shaped similarly or identically to a sample container. This can allow for the gripping device to handle the position determining device identically or similarly to a sample container for the purpose of position determination.

According to an embodiment, the method can further comprise placing the position determining device in the specified position relationship using the gripping device being performed before detecting the position. For example, the position determining device can be stored in the laboratory station or, in a case of an engineer being charged with configuring the laboratory automation system and can be used just for the case of definition of the handover position.

According to an embodiment, detecting the position can be performed after a, for example, manual, input to the control device indicating final placement of the laboratory station. This can provide for a high degree of certainty for the control device that the laboratory station and the corresponding reference magnet can be in their final and correct position.

A laboratory sample distribution system is also presented. The laboratory sample distribution system can comprise a number of sample container carriers adapted to carry one or more sample containers. Each sample container carrier can comprise at least one magnetically active device. The laboratory sample distribution system can further comprise a transport plane adapted to support the sample container carriers.

The laboratory sample distribution system can further comprise a number of electro-magnetic actuators stationary arranged below the transport plane. The electro-magnetic actuators can be adapted to move the sample container carriers on top of the transport plane by applying a magnetic drive or move force to the sample container carriers.

The laboratory sample distribution system can further comprise a number of position sensors, e.g. Hall sensors, distributed over the transport plane and adapted to sense magnetic fields generated by the magnetically active devices.

The laboratory sample distribution system can further comprise a control device configured to control the movement of the sample container carriers on top of the transport plane by driving the electro-magnetic actuators such that the sample container carriers can move along corresponding transport paths.

The control device of the laboratory sample distribution system can further be configured to perform a method as described above.

The control device can be embodied as a microprocessor, microcontroller, computer or other programmable device. The control device can, for example, comprise a processor and storage. Program code can be stored in the storage in order to make the control device to perform a method as described herein when executed by the processor.

The control device can be adapted to activate the electro-magnetic actuators such that the sample container carriers move simultaneously and independently from one another along pre-calculated routes.

A laboratory automation system is also presented. The laboratory automation system can comprise a laboratory sample distribution system and at least one laboratory station. With respect to the laboratory sample distribution system, all embodiments and variations as discussed herein can be applied.

A laboratory automation system is also presented, wherein the laboratory automation system can be configured using a method. With regard to the method, all embodiments and variations as discussed herein can be applied.

A laboratory station can be a pre-analytical, analytical and/or post-analytical (laboratory) station. The laboratory sample distribution system can be adapted to transport the sample container carriers and/or sample containers between the laboratory stations. The laboratory stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exist.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

It can be noted that after the handover electro-magnetic actuator has been identified, a further determination of the handover position with a significantly higher spatial resolution can be performed.

A gripping device can be assigned to a laboratory sample distribution system having a transport plane and a plurality of electro-magnetic actuators positioned below the transport plane. The handover position may be assigned to a handover electro-magnetic actuator. The determination of a handover position of the gripping device may be performed by a method comprising the following steps: grabbing, by the gripping device, a position determining device such that the position determining device can be held fixedly by the gripping device. The position determining device can comprise a magnetically active device. The method can also comprise positioning the position determining device, while being held by the gripping device, on (over) the transport plane, activating the handover electro-magnetic actuator such that it can generate a magnetic field interacting with a magnetic field generated by the magnetically active device such that an attractive force can be applied on the position determining device, moving the position determining device, while being held by the gripping device, by the attractive force to a first position, detecting the first position, and determining the handover position based at least in part on the first position.

According to an embodiment, the handover position can be determined as being identical to the first position.

According to an embodiment, determining the handover position can comprise moving the position determining device, by the gripping device, on the transport plane in each of a group of directions for a given amount of displacement, every time starting from the first position, to a respective intermediate position, after each step of moving in a direction, moving the position determining device while being held by the gripping device to a respective further position by the attractive force, detecting each respective further position, and determining the handover position based at least in part on the respective further positions.

According to an embodiment, the group of directions can comprise two, three or four directions.

According to an embodiment, all directions contained in the group of directions can be arranged with equal angle between each two circularly neighboring directions.

According to an embodiment, the given amount of displacement can be less than about 10 mm. According to another embodiment, the given amount of displacement can be less than about 5 mm. According to yet another embodiment, the given amount of displacement can be less than about 3 mm.

According to an embodiment, the handover position can be determined as a center of a polygon defined by the further positions.

According to an embodiment, the handover electro-magnetic actuator can be deactivated before each step of moving the position determining device in one of the directions and can be reactivated after that step.

According to an embodiment, the first position and/or the further positions can be represented by planar coordinates on the transport plane after being detected.

According to an embodiment, the step of positioning, by the gripping device, the position determining device on the transport plane can be performed such that the gripping device can be positioned over or besides the handover electro-magnetic actuator.

According to an embodiment, the step of positioning the position determining device, while being held by the gripping device, on the transport plane can be performed manually.

According to an embodiment, electro-magnetic actuators surrounding the handover electro-magnetic actuator can be activated such that they generate respective magnetic fields interacting with the magnetic field generated by the magnetically active device such that a repulsive force can be applied on the position determining device at least during each step of moving the position determining device by the attractive force.

According to an embodiment, the position determining device can comprise a number of rolls, or ball-bearings, for contacting the transport plane.

Referring initially to FIG. 1, FIG. 1 shows a laboratory automation system 10. The laboratory automation system 10 can comprise a laboratory station 20 and a laboratory sample distribution system 100. It may be noted that the laboratory station 20 is shown only exemplarily, and that typical laboratory automation systems can comprise a plurality of laboratory stations 20.

The laboratory sample distribution system 100 can comprise a transport plane 110. On the transport plane 110, sample container carriers 140 can move. A sample container carrier 140 can carry a sample container 145, which can be embodied as a typical laboratory sample tube. It can be noted that a typical laboratory sample distribution system 100 can comprise a plurality of sample container carriers 140, and that the single sample container carrier 140 is only shown exemplarily in FIG. 1.

Each sample container carrier 140 can comprise a magnetically active device in the form of a permanent magnet. The permanent magnet is not visible in FIG. 1 because it can be located inside the sample container carrier 140.

Under the transport plane 110, a plurality of electro-magnetic actuators 120 can be arranged. The electro-magnetic actuators 120 can be embodied as solenoids. Each electro-magnetic actuator 120 can comprise an associated ferromagnetic core 125. The electro-magnetic actuators 120 can be adapted to generate magnetic fields used to move the sample container carrier 140 over the transport plane 110.

The laboratory sample distribution system 100 can comprise a plurality of position sensors 130. The position sensors 130 can be distributed over the transport plane 110. The position sensors 130 can be embodied as Hall sensors and can measure the magnetic field generated by the permanent magnet of the sample container carrier 140.

Both the electro-magnetic actuators 120 and the position sensors 130 can be electrically connected to a control device 150. The control device 150 can be configured to drive the electro-magnetic actuators 120 such that they can generate appropriate magnetic fields in order to move the sample container carrier 140 over the transport plane along a corresponding transport path. By the position sensors 130, the control device 150 can monitor the actual position of the sample container carrier 140.

The laboratory station 20 can be positioned adjacent to the transport plane 110. The laboratory station 20 can comprise a gripping device 22. The gripping device 22 can typically be used for transfer of sample containers 145 between the laboratory station 20 and the transport plane 110. In the state shown in FIG. 1, the gripping device 22 can hold a position determining device 24. The current position of the position determining device 24 can define a handover position of the laboratory station 20.

The position determining device 24 can comprise a magnetically active device in the form of a permanent magnet. The permanent magnet can serve as a reference magnet and can be sensed by the position sensors 130 in the same way as the permanent magnet of the sample container carrier 140. Thus, the control device 150 can also be aware of the position of the reference magnet comprised in the position determining device 24.

After the laboratory station 20 has been placed adjacent to the transport plane 110, the laboratory automation system 10 can be configured as follows.

The gripping device 22 holding the position determining device 24 comprising the reference magnet can be placed at the desired handover position of the laboratory station 20 over the transport plane 110.

The control device 150 can comprise a button 152. The button 152 can be pressed by an operator when the laboratory station 20 has reached its final position adjacent to the transport plane 110.

After the control device 150 has detected that the button 152 has been pressed, the control device 150 can start the calibration of the laboratory automation system 10. If the reference magnet is embodied as an electromagnet, the electromagnet may be energized when the button 152 is pressed.

First, the control device 150 can detect the position of the reference magnet using the position sensors 130. In the depicted embodiment, the control device 150 can detect that the position determining device 24 (or the reference magnet of the position determining device 24) can be positioned over a specific one of the electro-magnetic actuators 120. Thus, the control device 150 can determine this specific electro-magnetic actuator as the handover electro-magnetic actuator 122. In case the reference magnet is not placed exactly over one of the electro-magnetic actuators 120, the handover electro-magnetic actuator 122 may be defined as the electro-magnetic actuator having a minimal distance to the reference magnet.

If the laboratory station 20 would have been placed at another position adjacent to the transport plane 110, the control device 150 can determined another handover electro-magnetic actuator accordingly. This can eliminate the need to place the laboratory station 20 at a predetermined position.

The control device 150 can move sample container carriers 140 to that handover electro-magnetic actuator 122 if a sample or a sample container 145 carried by the sample container carrier 140 is to be transferred to the laboratory station 20. Accordingly, a sample or a sample container 145 can be transferred from the laboratory station 20 using the handover electro-magnetic actuator 122.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of configuring a laboratory automation system, the laboratory automation system comprising a laboratory sample distribution system and at least one laboratory station, wherein the laboratory station has a handover position and the laboratory sample distribution system comprises a number of sample container carriers adapted to carry one or more sample containers, wherein each sample container carrier comprises at least one magnetically active device, a transport plane adapted to support the sample container carriers, a number of electro-magnetic actuators stationary arranged below the transport plane, the electro-magnetic actuators adapted to move sample container carriers on top of the transport plane by applying a magnetic force to the sample container carriers, a number of position sensors distributed over the transport plane and adapted to sense magnetic fields generated by the magnetically active devices, and a control device configured to control the movement of the sample container carriers on top of the transport plane by driving the electro-magnetic actuators such that the sample container carriers move along corresponding transport paths, wherein the laboratory station is placed adjacent to the transport plane, the method comprising:
   placing a reference magnet in a specified position relationship with the handover position of the laboratory station over the transport plane;
   detecting the position of the reference magnet on the transport plane using the position sensors; and
   determining one of the electro-magnetic actuators as a handover electro-magnetic actuator based on the detected position.

2. The method according to claim 1, wherein the position of the reference magnet is determined in the same way as a position of the sample container carriers.

3. The method according to claim 1, wherein the position of the reference magnet is determined by the control device.

4. The method according to claim 1, wherein the reference magnet is part of the laboratory station.

5. The method according to claim 1, wherein the reference magnet is part of a position determining device held by a gripping device of the laboratory station.

6. The method according to claim 5, further comprising, placing the position determining device in the specified position relationship using the gripping device before detecting the position.

7. The method according to claim 1, wherein detecting the position is performed after an input to the control device indicating final placement of the laboratory station.

8. The method according to claim 1, wherein the handover position is a position configured to transfer samples or sample containers between the laboratory station and the transport plane.

9. The method according to claim 1, wherein the handover electro-magnetic actuator is configured such that sample containers or sample container carriers are moved to the handover electro-magnetic actuator for transfer of samples or sample containers between the laboratory station and the transport plane.

10. A laboratory sample distribution system, the laboratory sample distribution system comprising:
    a number of sample container carriers adapted to carry one or more sample containers, wherein each sample container carrier comprises at least one magnetically active device;
    a transport plane adapted to support the sample container carriers;
    a number of electro-magnetic actuators stationary arranged below the transport plane, the electro-magnetic actuators adapted to move sample container carriers on top of the transport plane by applying a magnetic force to the sample container carriers;
    a number of position sensors distributed over the transport plane and adapted to sense magnetic fields generated by the magnetically active devices; and
    a control device configured to control the movement of the sample container carriers on top of the transport plane by driving the electro-magnetic actuators such that the sample container carriers move along corresponding transport paths, wherein the control device is configured to perform a method according to claim 1.

11. A laboratory automation system comprising a laboratory sample distribution system according to claim 10 and at least one laboratory station.

12. A laboratory automation system, wherein the laboratory automation system is configured using a method according to claim 1.

* * * * *